(12) United States Patent
Nzike et al.

(10) Patent No.: US 9,421,335 B2
(45) Date of Patent: Aug. 23, 2016

(54) DRIVE MECHANISM FOR A DRUG DELIVERY DEVICE AND DRUG DELIVERY DEVICE

(75) Inventors: Philippe Nzike, Frankfurt am Main (DE); Steffen Raab, Frankfurt am Main (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 468 days.

(21) Appl. No.: 13/883,394

(22) PCT Filed: Nov. 11, 2011

(86) PCT No.: PCT/EP2011/069963
§ 371 (c)(1),
(2), (4) Date: May 3, 2013

(87) PCT Pub. No.: WO2012/062912
PCT Pub. Date: May 18, 2012

(65) Prior Publication Data
US 2013/0231615 A1   Sep. 5, 2013

(30) Foreign Application Priority Data
Nov. 12, 2010 (EP) .................................. 10190942

(51) Int. Cl.
*A61M 5/315* (2006.01)
(52) U.S. Cl.
CPC ......... *A61M 5/3155* (2013.01); *A61M 5/31525* (2013.01); *A61M 5/31533* (2013.01); *A61M 5/31528* (2013.01)

(58) Field of Classification Search
CPC ............ A61M 5/3125; A61M 5/3155; A61M 5/31533; A61M 5/31528; A61M 5/3158
See application file for complete search history.

(56) References Cited

U.S. PATENT DOCUMENTS

2008/0234633 A1* 9/2008 Nielsen ......................... 604/208

FOREIGN PATENT DOCUMENTS

| DE | 10237258 B4 | 9/2006 |
| EP | 0615762 | 9/1994 |
| EP | 1728529 | 12/2006 |
| WO | 2006/084876 | 8/2006 |
| WO | 2007/017052 | 2/2007 |

OTHER PUBLICATIONS

International Search Report for Int. App. No. PCT/EP2011/069963, completed Feb. 27, 2012.

* cited by examiner

*Primary Examiner* — Nathan R Price
*Assistant Examiner* — Melissa A Snyder
(74) *Attorney, Agent, or Firm* — McDonnell Boehnen Hulbert & Berghoff LLP

(57) ABSTRACT

A drive sleeve is arranged within a body and coupled with a dose member by means of threads. Stop means inhibit a shift of the drive sleeve while allowing a rotation of the drive sleeve. A clutch is provided to lock the dose member rotationally to the body in a releasable manner when a force is exerted on the dose member in the distal direction, the clutch permitting a movement of the dose member in the distal direction with respect to the body.

14 Claims, 2 Drawing Sheets

DRIVE MECHANISM FOR A DRUG DELIVERY DEVICE AND DRUG DELIVERY DEVICE

CROSS REFERENCE TO RELATED APPLICATIONS

The present application is a U.S. National Phase Application pursuant to 35 U.S.C. §371 of International Application No. PCT/EP2011/069963 filed Nov. 11, 2011, which claims priority to European Patent Application No. 10190942.2 filed Nov. 12, 2010. The entire disclosure contents of these applications are herewith incorporated by reference into the present application.

FIELD OF DISCLOSURE

The present invention relates to a drive mechanism for a drug delivery device and a drug delivery device incorporating such a drive mechanism.

BACKGROUND

Portable drug delivery devices are used for the administration of a drug that is suitable for self-administration by a patient. A drug delivery device is especially useful in the shape of a pen, which can be handled easily and kept everywhere available. A type of drug delivery device is constructed to be refillable and reusable many times. A drug is delivered by means of a drive mechanism, which may also serve to set the dose or amount to be delivered.

DE 102 37 258 B4 describes a drug delivery device in the shape of an injection pen having a drive mechanism, which allows to deliver a plurality of different prescribed doses. The drive mechanism comprises elements which are rotated relatively to one another around a common axis. They are coupled by unidirectional gears.

SUMMARY

It is an object of the present invention to disclose a new drive mechanism for a drug delivery device that allows to set a dose.

This object is achieved by a drive mechanism according to claim 1. Further objects are achieved by variants and embodiments according to the dependent claims.

The drive mechanism for a drug delivery device comprises a body having a proximal end and a distal end, a dose member having a thread, and a drive sleeve. The drive sleeve is rotatable with respect to the body and has a thread which engages the thread of the dose member. Stop means restrict or inhibit a movement of the drive sleeve in the proximal direction and in the distal direction with respect to the body. A clutch is provided to lock the dose member rotationally to the body in a releasable manner when a force is exerted on the dose member in the distal direction, the clutch permitting a movement of the dose member in the distal direction with respect to the body.

The body can be any housing or any component that forms part of a housing, for example. The body can also be some kind of an insert connected with an exterior housing. The body may be designed to enable the safe, correct, and/or easy handling of the device and/or to protect it from harmful liquids, dust or dirt. The body can be unitary or a multipart component of tubular or non-tubular shape. The body may house a cartridge, from which doses of a drug can be dispensed. The body can especially have the shape of an injection pen. The term "distal end" refers to a part of the body or housing which is intended to be arranged at a portion of the drug delivery device from which a drug is dispensed. The term "proximal end" refers to a part of the body or housing which is remote from the distal end.

In an embodiment of the drive mechanism, the dose member has a cylindrical shape and partially surrounds the drive sleeve.

In an embodiment of the drive mechanism, the stop means are provided by webs or interfaces of the body.

Further embodiments comprise a clutch member, which is rotationally locked to the body. An axial coupling means and a rotational coupling means are provided at the clutch member and the dose member. The axial coupling means is provided to move the clutch member in the proximal direction when the dose member is moved in the proximal direction, and the rotational coupling means forms the clutch.

In a further embodiment the rotational coupling means comprises a surface of the clutch member and a surface of the dose member, the surfaces being coupled by friction.

In a further embodiment the rotational coupling means comprises a structured surface of the clutch member and a structured surface of the dose member, the structured surfaces mechanically engaging with one another.

Further embodiments comprise a piston rod arranged within the body, the piston rod being movable in distal direction and in proximal direction. The drive sleeve is rotationally coupled to the piston rod. The term "piston rod" encompasses any element that is provided to transfer a movement to a piston, especially for the purpose of dispensing a drug. The piston rod may be flexible or not. It may be of unitary or multipart construction, and may especially be a simple rod, a lead-screw, a rack-and-pinion, a worm gear system, or the like.

A further embodiment comprises a drive member rotationally locked to the piston rod and held in contact with the drive sleeve. The drive member permits the drive sleeve to rotate in one direction relatively to the piston rod and inhibits the drive sleeve from rotating in the opposite direction relatively to the piston rod.

A further embodiment comprises a stop member rotationally locked to the body and held in contact with the drive member. The stop member permits the drive member to rotate in one direction relatively to the body and inhibits the drive member from rotating in the opposite direction relatively to the body.

A further embodiment comprises a guide means coupled to the piston rod and restricting a relative movement of the piston rod with respect to the body to a helical movement.

In a further embodiment of the drive mechanism, a set operation is performed by a helical movement of the dose member with respect to the body in the proximal direction, the helical movement being guided by the thread of the dose member and the thread of the drive sleeve, while the drive sleeve is stationary with respect to the body.

In a further embodiment of the drive mechanism, a dispense operation is performed by a movement of the dose member with respect to the body in the distal direction. A rotation of the dose member with respect to the body is inhibited by the clutch, and a rotation of the drive sleeve with respect to the body is generated by the thread of the dose member and the thread of the drive sleeve.

In a further embodiment of the drive mechanism, a correcting set operation is performed by a helical movement of the dose member with respect to the body in the distal direction, the helical movement being guided by the thread of the dose member and the thread of the drive sleeve, while the drive sleeve is stationary with respect to the body.

The invention further relates to a drug delivery device with a drive mechanism according to one of the embodiments. The drug delivery device can especially have a body in the shape of an injection pen.

The drug delivery device can be a disposable or re-usable device designed to dispense a dose of a drug, especially a liquid, which may be insulin, a growth hormone, a heparin, or an analogue and/or a derivative thereof, for example. The device can be configured to dispense fixed doses of the drug or variable doses. The drug may be administered by a needle, or the device may be needle-free. The device may be further designed to monitor physiological properties like blood glucose levels, for example.

These and other features of the invention will become apparent from the following brief description of the drawings, detailed description and appended claims and drawings, in which similar or corresponding elements bear the same reference numerals.

DETAILED DESCRIPTION

Figure 1:
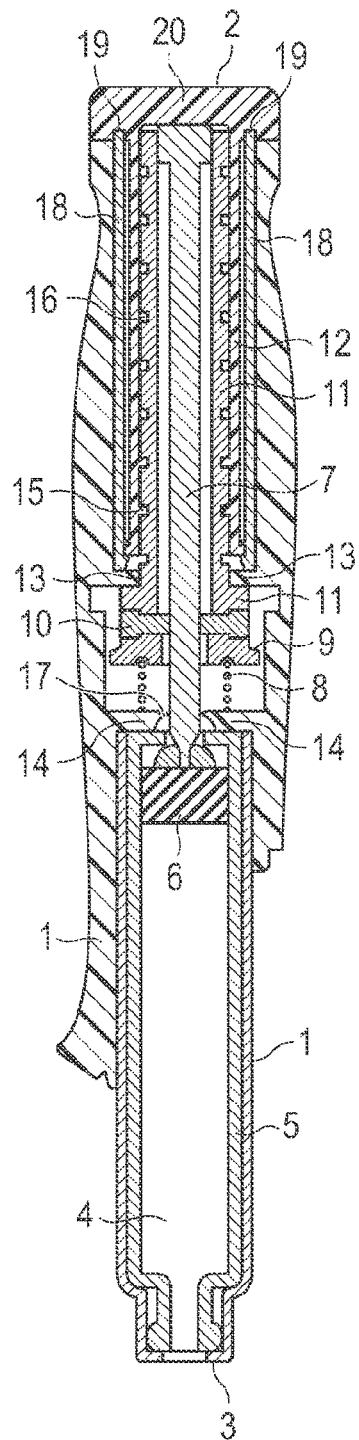
FIG. 1 shows a cross-section of an injection pen comprising an embodiment of the drive mechanism.

FIG. 1 shows a cross-section of a drug delivery device in the shape of an injection pen. The drug delivery device can have another suitable shape instead, according to the shape of a body or housing. The term "body" encompasses any exterior housing, like a main housing or shell, as well as an interior housing, like an insert or inner body arranged within an exterior housing. In the embodiment shown in FIG. 1, the body 1 is of elongated shape. It has a proximal end 2 and a distal end 3. The body 1 can be composed of at least two attachable and separable parts enabling a refill of the device.

The body 1 comprises a receptacle 4 for a drug. The receptacle 4 can be designed to be filled by means of a cartridge 5 containing the drug and being inserted in the receptacle 4. A full cartridge 5 preferably contains a plurality of doses of the drug. When the cartridge 5 is empty, it can be removed and substituted with a new cartridge.

The drug is dispensed through an opening of the receptacle 4 by means of a piston 6, which is advanced in the receptacle 4, particularly within the cartridge 5, towards the distal end 3 by means of a piston rod 7. The distal end 3 can be provided with a needle, not shown in FIG. 1, or with a needle unit, for instance.

If the piston rod 7 is to be moved relatively to the piston 6, a bearing, which is schematically shown in FIG. 1, can be arranged at the connection of the piston 6 with the piston rod 7 to reduce damages that may be caused by friction. The drive mechanism shown in FIG. 1 can be operated by means of a dose button 20 at the proximal end 2. The dose button 20 is located outside the body 1 and can be gripped by a user.

The drive mechanism comprises a drive sleeve 11, which is partially surrounded by a cylindrical dose member 12 provided with the dose button 20. The drive sleeve 11 and the dose member 12 are coupled by means of a thread 15 of the dose member 12 engaging a corresponding thread 16 of the drive sleeve 11. Because of the threads, the dose member 12 can be moved helically with respect to the drive sleeve 11. The drive sleeve 11 can be rotated with respect to the body 1, but a movement of the drive sleeve 11 in the distal direction or in the proximal direction is inhibited or at least restricted. To this purpose, the body 1 can be provided with stop means, which can be interfaces or webs 13, 14, for instance, which stop a shift of the drive sleeve 11 in the distal direction and in the proximal direction.

The movement of the piston rod 7 with respect to the body 1 is guided by a suitable guide means 17. The guide means 17 can be an integral part of the body 1, or it may be an element which is permanently or temporarily fastened to the body 1, like a nut, for example. The piston rod 7 passes through an opening of the guide means 17, which engages a thread of the piston rod 7 to restrict the movement of the piston rod 7 with respect to the body 1 to a helical movement. A rotation of the piston rod 7 with respect to the body 1 thus comprises a simultaneous shift of the piston rod 7 with respect to the body 1.

A clutch sleeve 18 comprising a clutch 19 is arranged between the body 1 and the dose member 12. The clutch 19 can be formed by a surface area of the clutch sleeve 18 and a corresponding surface area of the dose member 12, the surface areas touching each other when the dose member 12 is moved towards the distal end 3 and rotationally coupling the clutch sleeve 18 and the dose member 12 by means of friction. Instead, the clutch 19 can be formed by a structured surface area of the clutch sleeve 18 and a corresponding structured surface area of the dose member 12. The surface structure may comprise teeth, for instance. When the dose member 12 is moved towards the distal end 3, the structured surface areas engage with each other, thus coupling the clutch sleeve 18 and the dose member 12 rotationally. The clutch sleeve 18 is rotationally locked to the body 1, which may be achieved by an axial groove or track and a corresponding element, like a track, pin, peg, hook, spike or lug, which is guided by the groove or track, for instance.

The embodiment according to FIG. 1 further comprises a spring 8, a stop member 9, and a drive member 10, which can be substituted with other means to couple the piston rod 7 with the drive sleeve 11. The drive member 10 and the drive sleeve 11 are rotationally coupled by a ratchet, and so are the drive member 10 and the stop member 9. The stop member 9 is rotationally locked to the body 1, but is allowed to perform a reciprocating motion enabling the ratchets to engage and disengage during a rotation in the permitted direction. The stop member 9, the drive member 10, and the drive sleeve 11 are held in contact by the action of the spring 8, which is supported by the web 14 of the body 1.

The ratchets allow unidirectional rotations of the drive member 10 with respect to the stop member 9 and with respect to the drive sleeve 11. In both of these relative movements, the drive member 10 rotates in the same sense of rotation with respect to the proximal direction. This means that, depending on the sense of rotation of the drive sleeve 11 with respect to the body 1, either the drive sleeve 11 is rotationally locked to the drive member 10, which rotates together with the drive sleeve 11 relatively to the body 1 and to the stop member 9, or the drive sleeve 11 rotates relatively to the body 1 and to the drive member 10, which is rotationally locked to the stop member 9.

The drive member 10 essentially stays at its position within the body 1 and is rotationally locked to the piston rod 7, while the piston rod 7 is able to move axially with respect to the body 1 in the distal direction or in the proximal direction. Because of the guide means 17, a rotation of the piston rod 7 by means of the drive member 10 generates a helical movement of the piston rod 7 relatively to the body 1. The guide means 17 is provided to convert a rotation of the drive member 10 that is permitted by the stop member 9 into a helical movement of the piston rod 7 shifting the piston rod 7 in the distal direction.

An operation to set a dose is performed by a helical movement of the dose member 12 with respect to the body 1 in the proximal direction. The dose member 12 can be rotated by turning the dose button 20, the helical movement being guided by the thread of the dose member 12 engaging the thread of the drive sleeve 11. The drive sleeve 11 is stationary with respect to the body 1, because the drive sleeve 11 is in contact with the web 13 or with another suitable stop means of the body 1, which inhibits a shift of the drive sleeve 11 in the proximal direction. A premature rotation of the drive sleeve 11 according to the rotation of the dose member 12 is preferably inhibited in view of dose accuracy. This can be achieved, for example, by means of the friction between the surfaces of the drive sleeve 11 and the web 13 which touch one another; instead, these surfaces may be provided with a structure engaging the drive sleeve 11 with the web 13 to inhibit a relative rotation.

Figure 2:
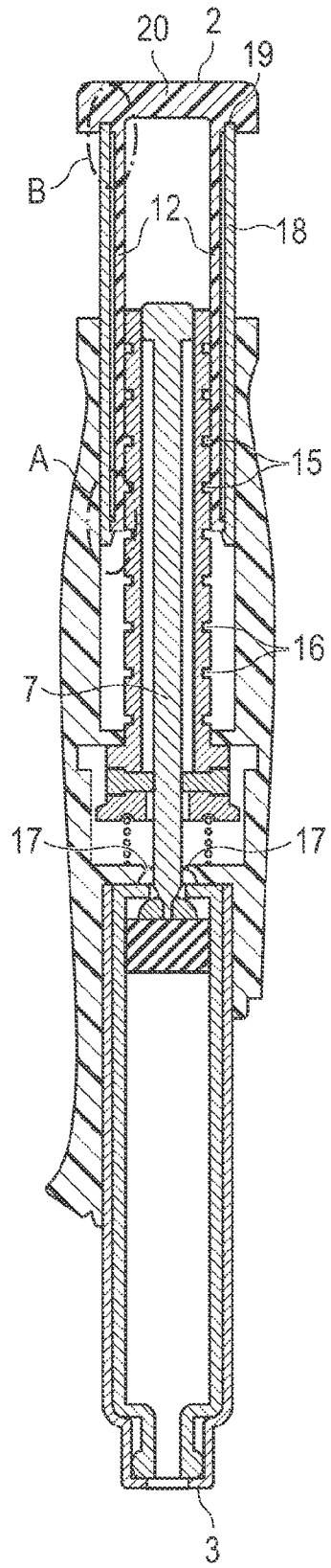
FIG. 2 shows a cross-section according to FIG. 1 after the setting of a dose.

FIG. 2 shows a cross-section of the drive mechanism after the setting of a dose. Further to the dose button 20, a portion of the dose member 12 now juts out of the body 1. An axial coupling means highlighted at letter A in FIG. 2 is provided to shift the clutch sleeve 18 in the proximal direction simultaneously with the dose member 12 to keep the clutch 19 ready for coupling the clutch sleeve 18 and the dose member 12. The clutch 19 thus forms a rotational coupling means highlighted at letter B in FIG. 2. Since the clutch sleeve 18 is rotationally locked to the body 1, the dose member 12 rotates relatively to the clutch sleeve 18 during the set operation. This is made possible by the clutch 19 not being engaged during the movement of the dose member 12 in the proximal direction.

A correction of the set dose is easily possible by a helical movement of the dose member 12 with respect to the body 1 in the distal direction. This is achieved by turning the dose button 20 in the opposite direction until the desired position of the dose member 12 is obtained. The correct value of the set dose may be indicated by a scale or a numbering applied to the dose member 12 or dose button 20. Audible and/or tactile means can also be provided to guide the user when setting a dose. When the dose member 12 is helically moved back in the distal direction, the helical movement of the dose member 12 with respect to the body 1 is again guided by the threads 15, 16 of the dose member 12 and the drive sleeve 11. A rotation of the drive sleeve 11 according to the rotation of the dose member 12 can be inhibited, in the described embodiment for example, by the coupling between the surfaces of the drive sleeve 11 and the web 13. A rotation of the drive sleeve 11 according to the rotation of the dose member 12 during the correction of the set dose may be allowed in embodiments comprising the arrangement of the spring 8, the stop member 9, and the drive member 10 as described above, because the stop member 9 inhibits an undesired rotation of the drive member 10 during the correction operation, even if the drive sleeve 11 rotates in the same sense as the dose member 12.

If the dose button 20 is not turned but pressed in the distal direction, the clutch 19 engages, and the dose member 12 and the clutch sleeve 18 are rotationally locked. This means that the dose member 12 cannot rotate with respect to the body 1, because the clutch sleeve 18 is rotationally locked to the body 1. The drive sleeve 11 is decoupled from the web 13 or other stop means and is free to rotate relatively to the body 1. A distal movement of the drive sleeve 11 is inhibited or restricted by a further stop means, which can be the web 14 or the stop member 9 under the load of the spring 8, for example. The shift of the dose member 12 with respect to the body 1 therefore requires a corresponding relative movement of the dose member 12 with respect to the drive sleeve 11. This movement can only be a helical relative movement because of the threads 15, 16 coupling the dose member 12 and the drive sleeve 11. The drive sleeve 11 is thus rotated with respect to the body 1. If the device is provided with the arrangement of the stop member 9 and the drive member 10, this rotation of the drive sleeve 11 locks the drive member 10 rotationally to the drive sleeve 11, and the drive member 10 is permitted to rotate in this sense of rotation. The drive member 10 therefore rotates according to the drive sleeve 11 and rotates the piston rod 7, which advances in the distal direction because of the guide means 17.

Figure 3:
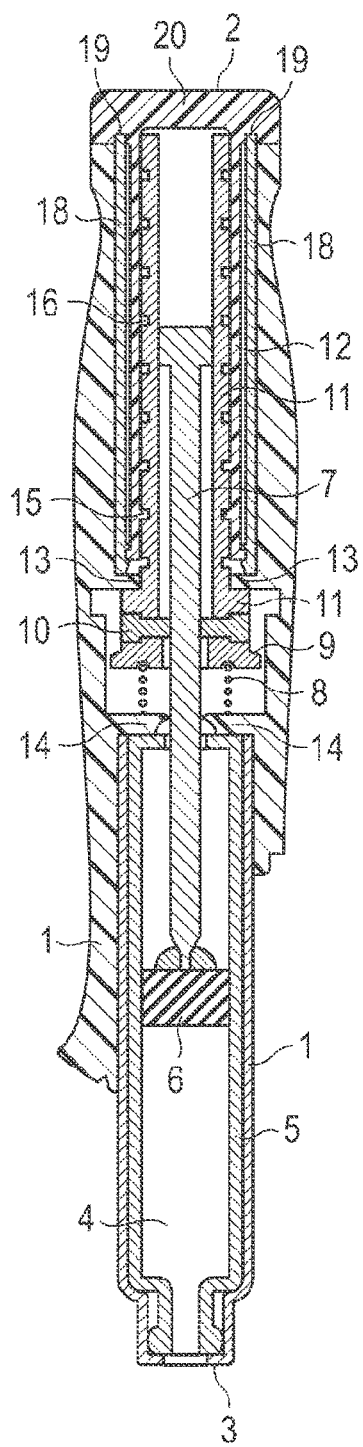
FIG. 3 shows a cross-section according to FIG. 1 after the delivery of several doses.

FIG. 3 shows a cross-section of the drive mechanism after the delivery of several doses. Apart from rotations, the dose member 12 is again in the position which it occupied when the device was in the initial state shown in FIG. 1. The position of the piston rod 7 is now changed, because the piston rod 7 was shifted several times in the distal direction in the course of delivery operations. The other components of the drive mechanism are arranged according to the state shown in FIG. 1, and a further set operation can be performed by turning the dose button 20 as described above.

The drive mechanism is easily and reliably operated and is therefore especially appropriate for drug delivery devices that are designed for repeated setting of doses, particularly varying doses. The drive mechanism allows a correction of the set dose in an easy way by just reversing the setting operation. It is an advantage of the drive mechanism that the accuracy in setting the dose is not adversely affected by a correction of the set dose. The correct use of the device is therefore assured, thus helping the user to administer the medication correctly.

The invention claimed is:

1. A drive mechanism for a drug delivery device, comprising:
   a body having a proximal end and a distal end,
   a dose member having a screw thread,
   a drive sleeve arranged within the body and being rotatable with respect to the body, the drive sleeve having a screw thread engaging the screw thread of the dose member,
   stop means comprising webs or interfaces of the body that restrict or inhibit a movement of the drive sleeve in the proximal direction and in the distal direction with respect to the body, and
   a clutch being provided to lock the dose member rotationally to the body in a releasable manner when a force is exerted on the dose member in the distal direction, the clutch permitting a movement of the dose member in the distal direction and a rotation of the drive sleeve with respect to the body.

2. The drive mechanism according to claim 1, wherein the dose member has a cylindrical shape and partially surrounds the drive sleeve.

3. The drive mechanism according to claim 1, further comprising:
   a clutch member rotationally locked to the body,
   an axial coupling means (A) at the clutch member and the dose member, the axial coupling means being provided to move the clutch member in the proximal direction when the dose member is moved in the proximal direction, and
   a rotational coupling means (B) at the clutch member and the dose member, the rotational coupling means forming the clutch.

4. The drive mechanism according to claim 3, wherein the rotational coupling means (B) comprises a surface of the clutch member and a surface of the dose member, the surfaces being coupled by friction.

5. The drive mechanism according to claim 3, wherein the rotational coupling means (B) comprises a structured surface of the clutch member and a structured surface of the dose member, the structured surfaces mechanically engaging with one another.

6. The drive mechanism according to claim 1, further comprising:
a piston rod arranged within the body, the piston rod being movable in distal direction and in proximal direction, the drive sleeve being rotationally coupled to the piston rod.

7. The drive mechanism according to claim 6, further comprising:
a drive member rotationally locked to the piston rod and held in contact with the drive sleeve, the drive member permitting a rotation of the drive sleeve in one direction relatively to the piston rod and inhibiting a rotation of the drive sleeve in the opposite direction relatively to the piston rod.

8. The drive mechanism according to claim 7, further comprising:
a stop member rotationally locked to the body and held in contact with the drive member, the stop member permitting a rotation of the drive member in one direction relatively to the body and inhibiting a rotation of the drive member in the opposite direction relatively to the body.

9. The drive mechanism according to claim 7, further comprising:
a guide means coupled to the piston rod, the guide means restricting a relative movement of the piston rod with respect to the body to a helical movement.

10. The drive mechanism according to claim 1, wherein a set operation is performed by a helical movement of the dose member with respect to the body in the proximal direction, the helical movement being guided by the screw thread of the dose member and the screw thread of the drive sleeve, and the drive sleeve being stationary with respect to the body.

11. The drive mechanism according to claim 1, wherein a dispense operation is performed by a movement of the dose member with respect to the body in the distal direction, a rotation of the dose member with respect to the body being inhibited by the clutch, a rotation of the drive sleeve with respect to the body being generated by the screw thread of the dose member and the screw thread of the drive sleeve.

12. The drive mechanism according to claim 1, wherein a correcting set operation is performed by a helical movement of the dose member with respect to the body in the distal direction, the helical movement being guided by the screw thread of the dose member and the screw thread of the drive sleeve, and the drive sleeve being stationary with respect to the body.

13. A drug delivery device, comprising a drive mechanism according claim 1.

14. The drug delivery device according to claim 13, wherein the body has a shape of an injection pen.

* * * * *